United States Patent
Hartley et al.

(10) Patent No.: US 6,351,669 B1
(45) Date of Patent: Feb. 26, 2002

(54) CARDIAC RHYTHM MANAGEMENT SYSTEM PROMOTING ATRIAL PACING

(75) Inventors: Jesse W. Hartley, Lino Lakes; Andrew P. Kramer, Stillwater; Jeffrey E. Stahmann, Ramsey; David B. Krig, Brooklyn Park, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/316,682

(22) Filed: May 21, 1999

(51) Int. Cl.[7] .................................................. A61N 1/18

(52) U.S. Cl. .................................................... 607/5

(58) Field of Search .......................... 607/5, 9, 14, 17, 607/25

(56) References Cited

U.S. PATENT DOCUMENTS

| | | | |
|---|---|---|---|
| 3,857,399 A | 12/1974 | Zacouto | 128/419 P |
| 4,030,510 A | 6/1977 | Bowers | 128/419 PG |
| 4,163,451 A | 8/1979 | Lesnick et al. | 128/419 PG |
| 4,556,063 A | 12/1985 | Thompson et al. | 128/419 PT |
| 4,830,006 A | 5/1989 | Haluska et al. | 128/419 PG |
| 4,917,115 A | 4/1990 | Flammang et al. | 128/419 PG |
| 4,920,965 A | 5/1990 | Funke et al. | 128/419 PG |
| 4,928,688 A | 5/1990 | Mower | 128/419 PG |
| 4,998,974 A | 3/1991 | Aker | 128/419 PG |
| 5,085,215 A | 2/1992 | Nappholz et al. | 128/419 PG |
| 5,127,404 A | 7/1992 | Wyborny et al. | 128/419 P |
| 5,129,394 A | 7/1992 | Mehra | 128/419 PG |
| 5,139,020 A | 8/1992 | Koestner et al. | 128/419 PG |
| 5,156,154 A | 10/1992 | Valenta, Jr. et al. | 128/661.09 |
| 5,183,040 A | 2/1993 | Nappholz et al. | 128/419 PG |
| 5,188,106 A | 2/1993 | Nappholz et al. | 128/419 PG |

(List continued on next page.)

FOREIGN PATENT DOCUMENTS

| | | | |
|---|---|---|---|
| EP | 0033418 | 12/1980 | A61N/1/36 |
| WO | 97/11745 | 4/1997 | A61N/1/362 |
| WO | 98/48891 | 11/1998 | A61N/1/362 |

OTHER PUBLICATIONS

*Harmony, Automatic Dual Chamber Pacemaker, Product Information and Programming Guide*, Viatron Medical, 22 p., (Date Unknown), Harmony Dual Chamber mentioned in publication Clinica, 467, p. 16, Sep. 11, 1991, "Rate Devices Impact Pacemaker Market", and Clinica, 417, p. 9, Sep. 5, 1990, "French CNH Equipment Approvals".

*Metrix Model 3020 Implantable Atrial Defibrillator*, Physician's Manual, InControl, Inc., Redmond, WA, pp. 4–24–4–27, (1998).

(List continued on next page.)

Primary Examiner—William E. Kamm
(74) Attorney, Agent, or Firm—Schwegman, Lundberg, Woessner & Kluth, P.A.

(57) ABSTRACT

A cardiac rhythm management system includes an atrial pacing preference (APP) filter for promoting atrial pacing. The APP filter includes an infinite impulse response (IIR) or other filter that controls the timing of delivery of atrial pacing pulses. The atrial pacing pulses are delivered at an APP-indicated pacing rate that is typically at a small amount above the intrinsic atrial heart rate. For sensed beats, the APP indicated rate is increased until it becomes slightly faster than the intrinsic atrial heart rate. The APP-indicated pacing rate is then gradually decreased to search for the underlying intrinsic atrial heart rate. Then, after a sensed atrial beat, the APP filter again increases the pacing rate until it becomes faster than the intrinsic atrial rate by a small amount. As a result, most atrial heart beats are paced, rather than sensed. This decreases the likelihood of the occurrence of an atrial tachyarrhythmia, such as atrial fibrillation. The decreased likelihood of atrial tachyarrhythmia, in turn, decreases the likelihood of inducing a ventricular arrhythmia, either as a result of the atrial tachyarrhythmia, or as the result of delivering a defibrillation shock to treat the atrial tachyarrhythmia.

37 Claims, 12 Drawing Sheets

U.S. PATENT DOCUMENTS

| | | | | |
|---|---|---|---|---|
| 5,207,219 A | | 5/1993 | Adams et al. | 128/419 D |
| 5,282,836 A | | 2/1994 | Kreyenhagen et al. | 607/4 |
| 5,284,491 A | | 2/1994 | Sutton et al. | 607/17 |
| 5,292,339 A | | 3/1994 | Stephens et al. | 607/15 |
| 5,312,452 A | | 5/1994 | Salo | 607/17 |
| 5,331,966 A | | 7/1994 | Bennett et al. | 128/696 |
| 5,350,409 A | | 9/1994 | Stoop et al. | 607/17 |
| 5,365,932 A | | 11/1994 | Greenhut | 128/696 |
| 5,383,910 A | | 1/1995 | den Dulk | 607/14 |
| 5,391,189 A | * | 2/1995 | van Krieken et al. | 607/17 |
| 5,395,397 A | | 3/1995 | Lindgren et al. | 607/9 |
| 5,400,796 A | | 3/1995 | Wecke | 128/705 |
| 5,411,524 A | | 5/1995 | Rahul | 607/4 |
| 5,411,531 A | | 5/1995 | Hill et al. | 607/14 |
| 5,417,714 A | | 5/1995 | Levine et al. | 607/9 |
| 5,462,060 A | | 10/1995 | Jacobson et al. | 128/702 |
| 5,480,413 A | | 1/1996 | Greenhut et al. | 607/14 |
| 5,486,198 A | | 1/1996 | Ayers et al. | 607/5 |
| 5,487,752 A | | 1/1996 | Salo et al. | 607/17 |
| 5,507,782 A | | 4/1996 | Kieval et al. | 607/9 |
| 5,507,784 A | | 4/1996 | Hill et al. | 607/14 |
| 5,514,163 A | | 5/1996 | Markowitz et al. | 607/9 |
| 5,522,859 A | | 6/1996 | Stroebel et al. | 607/19 |
| 5,527,347 A | | 6/1996 | Shelton et al. | 607/9 |
| 5,534,016 A | | 7/1996 | Boute | 607/9 |
| 5,540,727 A | | 7/1996 | Tockman et al. | 607/18 |
| 5,545,186 A | | 8/1996 | Olson et al. | 607/14 |
| 5,560,369 A | | 10/1996 | McClure et al. | 128/704 |
| 5,584,864 A | | 12/1996 | White | 607/5 |
| 5,584,867 A | | 12/1996 | Limousin et al. | 607/9 |
| 5,626,620 A | | 5/1997 | Kieval et al. | 607/9 |
| 5,626,623 A | | 5/1997 | Kieval et al. | 607/23 |
| 5,632,267 A | | 5/1997 | Högnelid et al. | 607/5 |
| 5,674,255 A | | 10/1997 | Walmsley et al. | 607/14 |
| 5,690,689 A | | 11/1997 | Sholder | 607/24 |
| 5,700,283 A | | 12/1997 | Salo | 607/17 |
| 5,713,929 A | | 2/1998 | Hess et al. | 607/14 |
| 5,713,932 A | | 2/1998 | Gillberg et al. | 607/27 |
| 5,716,383 A | | 2/1998 | Kieval et al. | 607/9 |
| 5,725,561 A | | 3/1998 | Stroebel et al. | 607/9 |
| 5,730,141 A | | 3/1998 | Fain et al. | 128/705 |
| 5,730,142 A | | 3/1998 | Sun et al. | 128/705 |
| 5,738,096 A | | 4/1998 | Ben-Haim | 128/653.1 |
| 5,741,308 A | | 4/1998 | Sholder | 607/9 |
| 5,749,906 A | | 5/1998 | Kieval et al. | 607/9 |
| 5,755,736 A | | 5/1998 | Gillberg et al. | 607/4 |
| 5,755,737 A | | 5/1998 | Prieve et al. | 607/4 |
| 5,776,164 A | | 7/1998 | Ripart | 607/5 |
| 5,776,167 A | | 7/1998 | Levine et al. | 607/9 |
| 5,788,717 A | | 8/1998 | Mann et al. | 607/14 |
| 5,800,464 A | | 9/1998 | Kieval | 607/9 |
| 5,800,471 A | | 9/1998 | Baumann | 607/25 |
| 5,814,077 A | | 9/1998 | Sholder et al. | 607/9 |
| 5,814,085 A | | 9/1998 | Hill | 607/14 |
| 5,836,975 A | | 11/1998 | DeGroot | 607/5 |
| 5,836,987 A | | 11/1998 | Baumann et al. | 607/17 |
| 5,846,263 A | | 12/1998 | Peterson et al. | 607/14 |
| 5,855,593 A | | 1/1999 | Olson et al. | 607/9 |
| 5,861,007 A | | 1/1999 | Hess et al. | 607/9 |
| 5,873,895 A | | 2/1999 | Sholder et al. | 607/9 |
| 5,873,897 A | | 2/1999 | Armstrong et al. | 607/14 |
| 5,893,882 A | | 4/1999 | Peterson et al. | 607/14 |
| 5,897,575 A | | 4/1999 | Wickham | 607/4 |
| 5,928,271 A | | 7/1999 | Hess et al. | 607/14 |
| 5,931,857 A | | 8/1999 | Prieve et al. | 607/14 |
| 5,935,081 A | | 8/1999 | Kadhiresan | 600/513 |
| 5,944,744 A | | 8/1999 | Paul et al. | 607/9 |
| 5,951,592 A | | 9/1999 | Murphy | 607/4 |
| 5,978,707 A | | 11/1999 | Krig et al. | 607/14 |
| 5,978,710 A | | 11/1999 | Prutchi et al. | 607/17 |
| 5,983,138 A | | 11/1999 | Kramer | 607/9 |
| 5,987,356 A | | 11/1999 | DeGroot | 607/5 |
| 5,991,656 A | | 11/1999 | Olson et al. | 607/4 |
| 5,999,850 A | | 12/1999 | Dawson et al. | 607/4 |
| 6,026,320 A | | 2/2000 | Carlson et al. | 600/510 |
| 6,044,298 A | | 3/2000 | Salo et al. | 607/17 |
| 6,049,735 A | | 4/2000 | Hartley et al. | 607/9 |
| 6,052,620 A | | 4/2000 | Gillberg et al. | 607/4 |
| 6,081,745 A | | 6/2000 | Mehra | 607/4 |

OTHER PUBLICATIONS

Ayers, G.M., et al., "Ventricular Proarrhythmic Effects of Ventricular Cycle Length and Shock Strength in a Sheep Model of Transvenous Atrial Defibrillation", *Circulation, 89 (1)*, pp. 413–422, (Jan. 1994).

Duckers, H.J., et al., "Effective use of a novel rate–smoothing algorithm in atrial fibrillation by ventricular pacing", *European Heart Journal, 18*, pp. 1951–1955, (1997).

Fahy, G.J., et al., "Pacing Strategies to Prevent Atrial Fibrillation", *Atrial Fibrillation, 14 (4)*, pp. 591–596, (Nov. 1996).

Greenhut, S., et al., "Effectiveness of a Ventricular Rate Stabilization Algorithm During Atrial Fibrillation in Dogs", *Pace*, Abstract, 1 p., (1996).

Heuer, H., et al., "Dynamic Dual–Chamber Overdrive Pacing with an Implantable Pacemaker System: A New Method for Terminating Slow Ventricular Tachycardia", *Zeitschrift fur Kardiologie, 75*, German Translation by the Ralph McElroy Translation Company, Austin, TX, 5 p., (1986).

Wittkampf, F., et al., "Rate Stabilization by Right Ventricular Pacing in Patients with Atrial Fibrillation", *Pace, 9*, pp. 1147–1153, (1986).

Mehra, R. et al., "Prevention of Atrial Fibrillation/Flutter by Pacing Techniques", *Interventional Electrophysiology, Second Edition*, Chapter 34, Futura Publishing Company, Inc., pp. 521–544 (1996).

* cited by examiner

CARDIAC RHYTHM MANAGEMENT SYSTEM PROMOTING ATRIAL PACING

CROSS REFERENCE TO RELATED APPLICATIONS

This application is related to the following co-pending, commonly assigned patent applications: "Method and Apparatus for Treating Irregular Ventricular Contractions Such as During Atrial Arrhythmia," U.S. Ser. No. 09/316,515; "Cardiac Rhythm Management System With Atrial Shock Timing Optimization," U.S. Ser. No. 09/316,741; and "System Providing Ventricular Pacing and Biventricular Coordination," U.S. Ser. No. 09/316,588; each of which are filed on even date herewith, each of which disclosure is herein incorporated by reference in its entirety.

TECHNICAL FIELD

This invention relates generally to cardiac rhythm management systems and particularly, but not by way of limitation, to a cardiac rhythm management system promoting atrial pacing.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation shock. The shock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management systems is the proper treatment of atrial tachyarrhythmias, such as atrial fibrillation. Atrial fibrillation is a common cardiac arrhythmia which reduces the pumping efficiency of the heart, though not to as great a degree as in ventricular fibrillation. However, this reduced pumping efficiency requires the ventricle to work harder, which is particularly undesirable in sick patients that cannot tolerate additional stresses. As a result of atrial fibrillation, patients must typically limit their activity and exercise.

Although atrial fibrillation, by itself, is usually not life-threatening, prolonged atrial fibrillation may be associated with strokes, which are thought to be caused by blood clots forming in areas of stagnant blood flow. Treating such blood clots requires the use of anticoagulants. Atrial fibrillation may also cause pain, dizziness, and other irritation to the patient. For this reason, atrial fibrillation is typically treated with a low energy defibrillation shock to enable the resumption of normal atrial heart rhythms.

An even more serious problem, however, is the risk that atrial fibrillation may induce irregular ventricular heart rhythms by processes that are yet to be fully understood. Such induced ventricular arrhythmias compromise pumping efficiency even more drastically than atrial arrhythmias and, in some instances, may be life-threatening. Moreover, treating atrial fibrillation by a defibrillation shock may also induce dangerous ventricular arrhythmias. For these and other reasons, there is a need for safe and more effective atrial therapy that prevents the occurrence of atrial tachyarrhythmias, such as atrial fibrillation, thereby avoiding inducing ventricular arrhythmia as the result of the atrial tachyarrhythmia or its treatment.

SUMMARY

This document discloses, among other things, a cardiac rhythm management system including an atrial pacing preference (APP) filter for promoting atrial pacing. The APP filter controls the timing of delivery of atrial pacing pulses. The atrial pacing pulses are delivered at a first indicated pacing rate, i.e., the APP-indicated rate, that is typically at a small amount above the intrinsic atrial heart rate. For sensed beats, the APP-indicated rate is increased until it becomes slightly faster than the intrinsic atrial heart rate of the sensed atrial beat. The APP-indicated pacing rate is then gradually decreased to search for the underlying intrinsic atrial heart rate. Then, after a sensed atrial beat, the APP filter again elevates the APP-indicated pacing rate until it is above the intrinsic heart atrial rate by a small amount. As a result, most atrial heart beats are paced, rather than sensed. This is believed to decrease the likelihood of the occurrence of an atrial tachyarrhythmia, such as atrial fibrillation. The decreased likelihood of atrial tachyarrhythmia, in turn, decreases the likelihood of inducing a ventricular arrhythmia, either as a result of the atrial tachyarrhythmia, or as the result of delivering a defibrillation shock to treat the atrial tachyarrhythmia.

In one embodiment, the cardiac rhythm management system includes a method comprising: (1) obtaining A-A intervals between atrial beats, (2) computing a first indicated pacing interval based at least on a most recent A-A interval duration and a previous value of the first indicated pacing interval, and (3) providing atrial pacing therapy, based on the first indicated pacing interval.

In another embodiment, the cardiac rhythm management system includes an atrial sensing circuit, an atrial therapy circuit, and a controller. The controller includes an A-A interval timer, a first register, for storing a first indicated pacing interval, and a filter, updating the first indicated pacing interval based on the A-A interval timer and the first register. The atrial therapy circuit provides pacing therapy based at least partially on the first indicated pacing interval. Other aspects of the invention will be apparent on reading the following detailed description of the invention and viewing the drawings that form a part thereof, each of which are not to be taken in a limiting sense; the scope of the present invention is defined by the appended claims and their equivalents.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
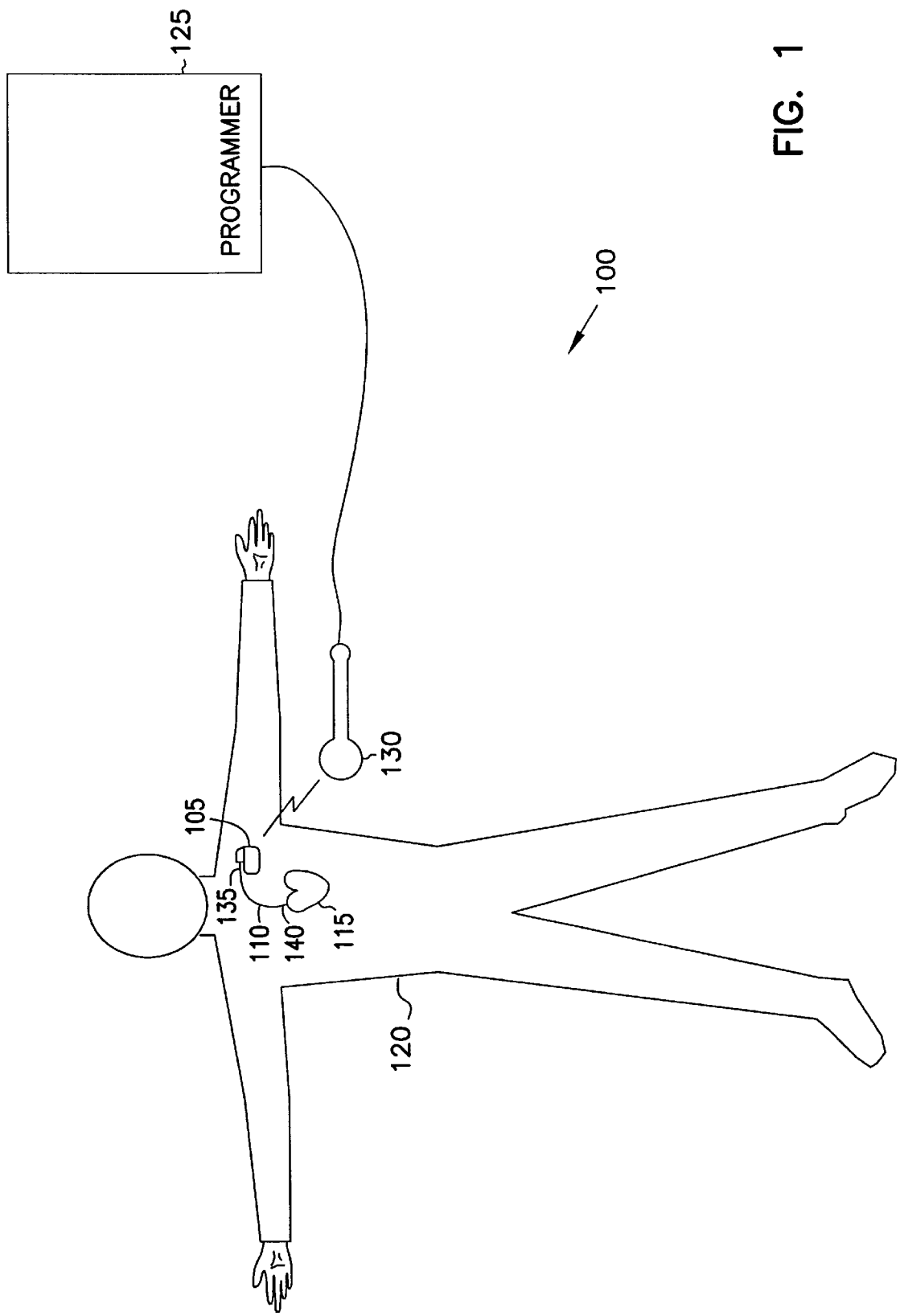
FIG. 1 is a schematic drawing illustrating one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

General Overview

This document describes, among other things, a cardiac rhythm management system including an atrial pacing preference (APP) filter for promoting atrial pacing over atrial sensing. The APP filter controls the timing of delivery of atrial pacing pulses. The atrial pacing pulses are delivered at a first indicated pacing rate, i.e., the APP-indicated pacing rate, that is typically at a small amount above the intrinsic atrial heart rate. The APP-indicated rate is slowly decreased to search for the underlying intrinsic atrial heart rate. Then, after a sensed atrial beat, the APP filter increases the pacing rate until it becomes faster than the intrinsic atrial rate by a small amount. As a result, most atrial heart beats are paced, rather than sensed. This decreases the likelihood of the occurrence of an atrial tachyarrhythmia, such as atrial fibrillation. The decreased likelihood of atrial tachyarrhythmia, in turn, decreases the likelihood of inducing a ventricular arrhythmia, either as a result of the atrial tachyarrhythmia, or as the result of delivering a defibrillation shock to treat the atrial tachyarrhythmia.

Example Embodiments

FIG. 1 is a schematic drawing illustrating, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
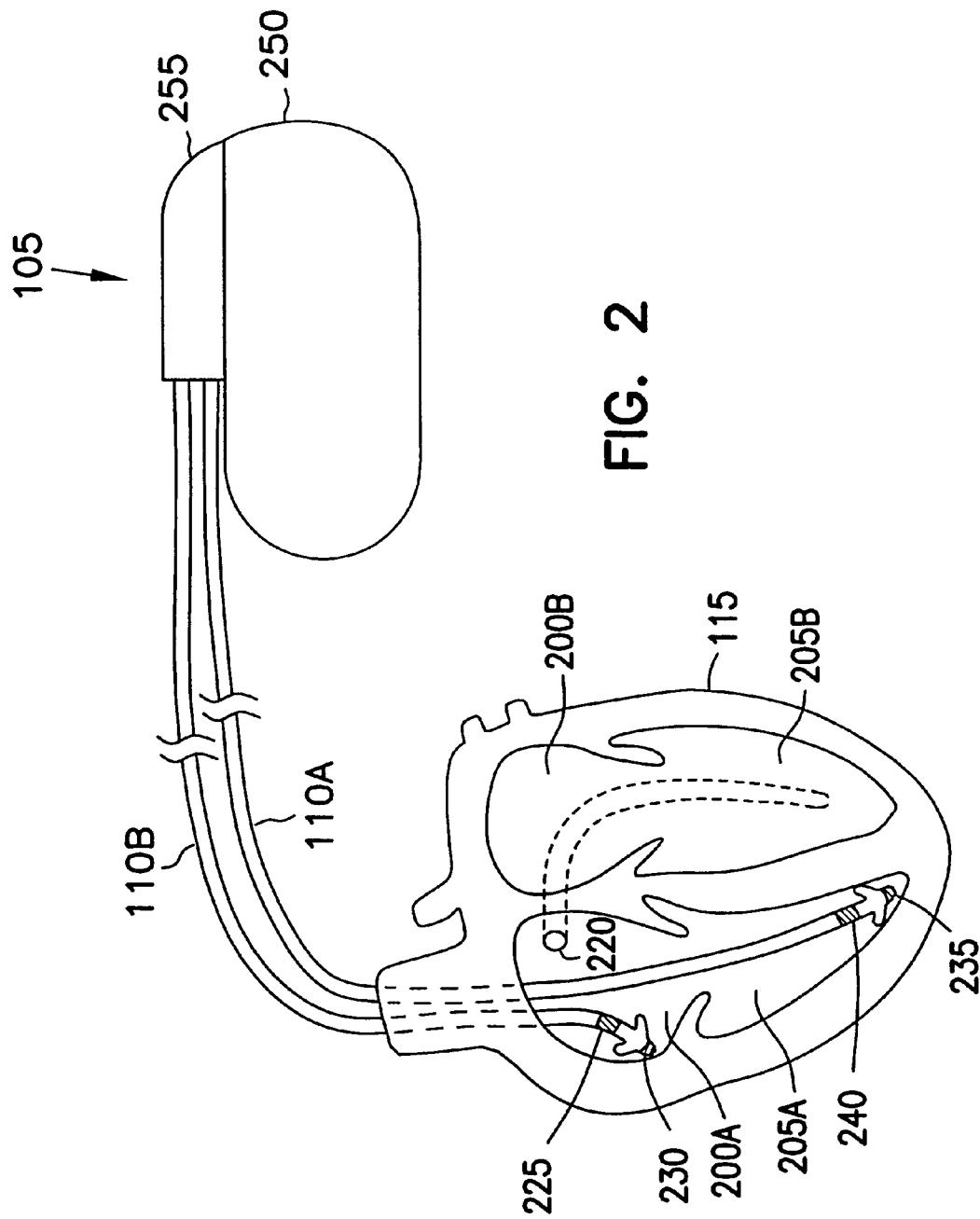
FIG. 2 is a schematic drawing illustrating one embodiment of a cardiac rhythm management device coupled by leads to portions of a heart.

FIG. 2 is a schematic drawing illustrating, by way of example, but not by way of limitation, one embodiment of device 105 coupled by one or more leads, such as leads 110A–B, to heart 115, which includes a right atrium 200A, a left atrium 200B, a right ventricle 205A, a left ventricle 205B, and a coronary sinus 220 extending from right atrium 200A. In this embodiment, atrial lead 110A includes electrodes (electrical contacts) disposed in, around, or near right atrium 200A of heart 115, such as ring electrode 225 and tip electrode 230, for sensing signals and/or delivering pacing therapy to the right atrium 200A. Lead 110A optionally also includes additional electrodes, such as for delivering atrial and/or ventricular cardioversion/defibrillation and/or pacing therapy to heart 115.

In FIG. 2, a ventricular lead 110B includes one or more electrodes, such as tip electrode 235 and ring electrode 240, for sensing signals and/or delivering pacing therapy. Lead 110B optionally also includes additional electrodes, such as for delivering atrial and/or ventricular cardioversion/defibrillation and/or pacing therapy to heart 115. Device 105 includes components that are enclosed in a hermetically-sealed can 250. Additional electrodes may be located on the can 250, or on an insulating header 255, or on other portions of device 105, for providing unipolar pacing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. The present method and apparatus will work in a variety of configurations and with a variety of electrical contacts or "electrodes."

Example Cardiac Rhythm Management Device

Figure 3:
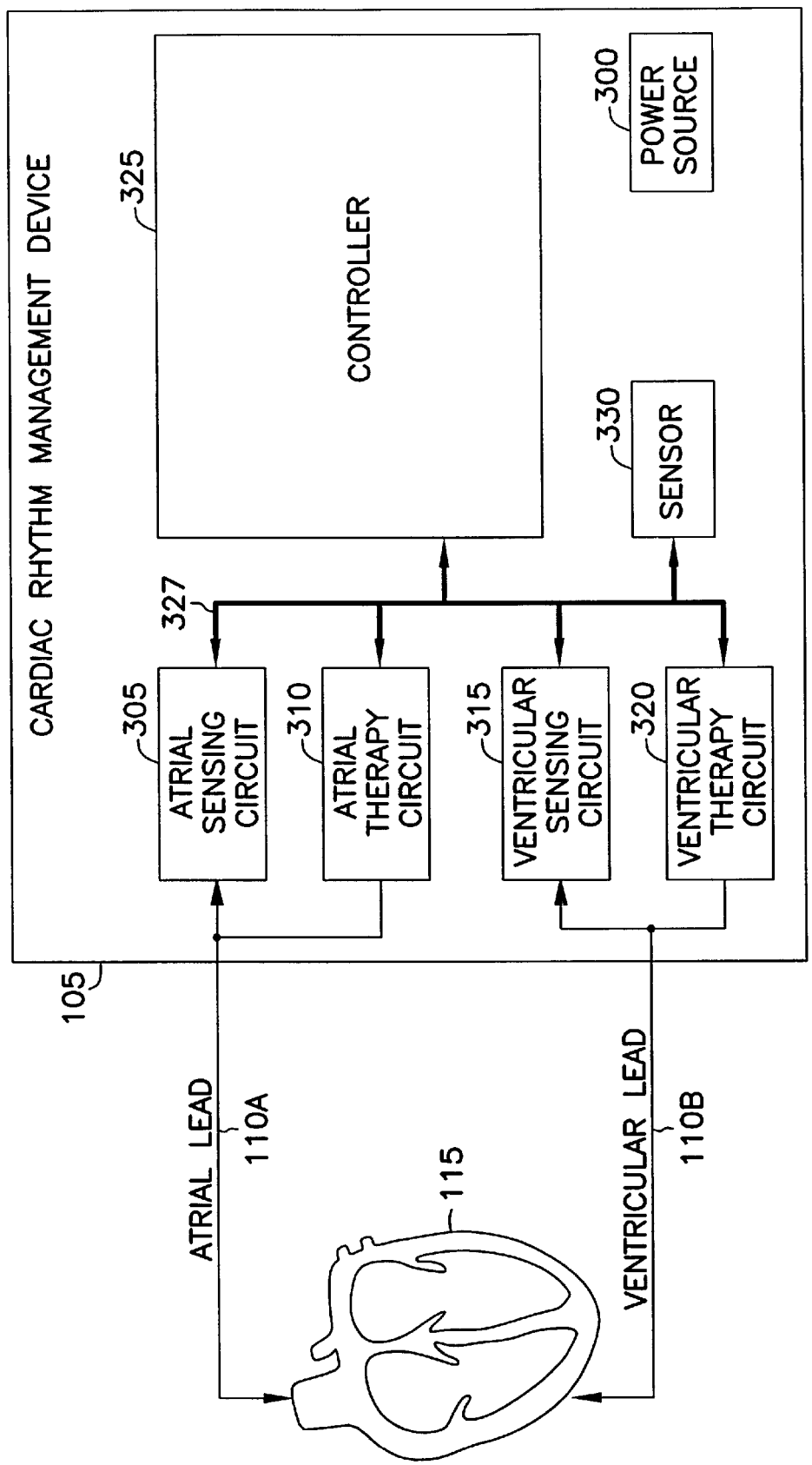
FIG. 3 is a schematic diagram illustrating generally one embodiment of portions of a cardiac rhythm management device which is coupled to a heart.

FIG. 3 is a schematic diagram illustrating generally, by way of example, but not by way of limitation, one embodiment of portions of device 105, which is coupled to heart 115. Device 105 includes a power source 300, an atrial sensing circuit 305, an atrial therapy circuit 310, and a controller 325. Device 105 also optionally includes a ventricular sensing circuit 315 and a ventricular therapy circuit 320.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals. Such signals provided to controller 325 indicate, among other things, the presence of sensed intrinsic atrial heart contractions.

Atrial therapy circuit 310 provides atrial pacing therapy, as appropriate, to electrodes located at or near one of the atria 200 of heart 115 for obtaining resulting evoked atrial depolarizations. In one embodiment, atrial therapy circuit 310 also provides cardioversion/defibrillation therapy, as appropriate, to electrodes located at or near one of the atria 200 of heart 115, for terminating atrial fibrillation and/or other atrial tachyarrhythmias.

Ventricular sensing circuit 315 is coupled by ventricular lead 110B to heart 115 for receiving, sensing, and/or detecting electrical ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Ventricular sensing circuit 315 provides one or more signals to controller 325, via node/bus 327, based on the received ventricular heart signals. Such signals provided to controller 325 indicate, among other things, the presence of ventricular depolarizations, whether regular or irregular in rhythm.

Ventricular therapy circuit 320 provides ventricular pacing therapy, as appropriate, to electrodes located at or near one of the ventricles 205 of heart 115 for obtaining resulting evoked ventricular depolarizations. In one embodiment, ventricular therapy circuit 320 also provides cardioversion/defibrillation therapy, as appropriate, to electrodes located at or near one of the ventricles 205 of heart 115, for terminating ventricular fibrillation and/or other ventricular tachyarrhythmias.

Controller 325 controls the delivery of therapy by atrial therapy circuit 310, ventricular therapy circuit 320, and/or other circuits, based on heart activity signals received from atrial sensing circuit 305 and ventricular sensing circuit 315, as discussed below. Controller 325 includes various modules, which are implemented either in hardware or as one or more sequences of steps carried out on a microprocessor or other controller. Such modules are illustrated separately for conceptual clarity; it is understood that the various modules of controller 325 need not be separately embodied, but may be combined and/or otherwise implemented, such as in software/firmware.

In general terms, sensing circuits 305 and 310 sense electrical signals from heart tissue in contact with the catheter leads 110A–B to which these sensing circuits 305 and 310 are coupled. Sensing circuits 305 and 310 and/or controller 325 process these sensed signals. Based on these sensed signals, controller 325 issues control signals to therapy circuits, such as atrial therapy circuit 310 and/or ventricular therapy circuit 320, if necessary, for the delivery of electrical energy (e.g., pacing and/or defibrillation pulses) to the appropriate electrodes of leads 110A–B. Controller 325 may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In one further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

Figure 4:
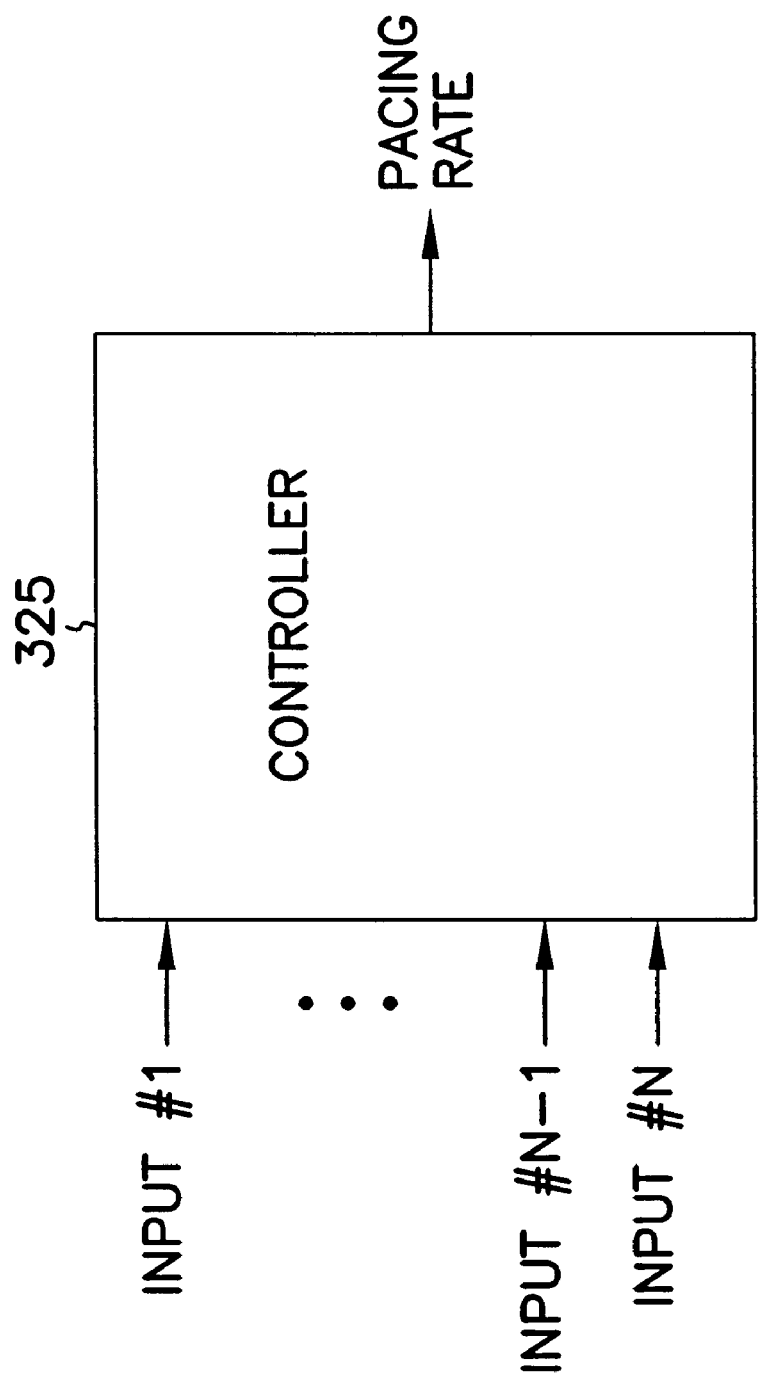
FIG. 4 is a schematic diagram illustrating generally one embodiment of a controller that includes several different inputs to modify the rate at which pacing or other therapy is delivered.

FIG. 4 is a schematic diagram illustrating generally, by way of example, but not by way of limitation, one embodiment of controller 325 that includes several different inputs to modify the rate at which pacing or other therapy is delivered. For example, Input#1 may provide information about atrial heart rate, Input #2 may provide information about ventricular heart rate, Input #3 may provide an accelerometer-based indication of activity, and Input #4 may provide an impedance-based indication of respiration, such as minute ventilation. Based on at least one of these and/or other inputs, controller 325 provides an output indication of pacing rate as a control signal delivered to a therapy circuit, such as to one or more of atrial therapy circuit 310 and ventricular therapy circuit 320. Atrial therapy circuit 310 and ventricular therapy circuit 320 issue pacing pulses based on one or more such control signals received from controller 325. Control of the pacing rate may be performed by controller 325, either alone or in combination with peripheral circuits or modules, using software, hardware, firmware, or any combination of the like. The software embodiments provide flexibility in how inputs are processed and may also provide the opportunity to remotely upgrade the device software while still implanted in the patient without having to perform surgery to remove and/or replace the device 105.

Controller Example 1

Figure 5:
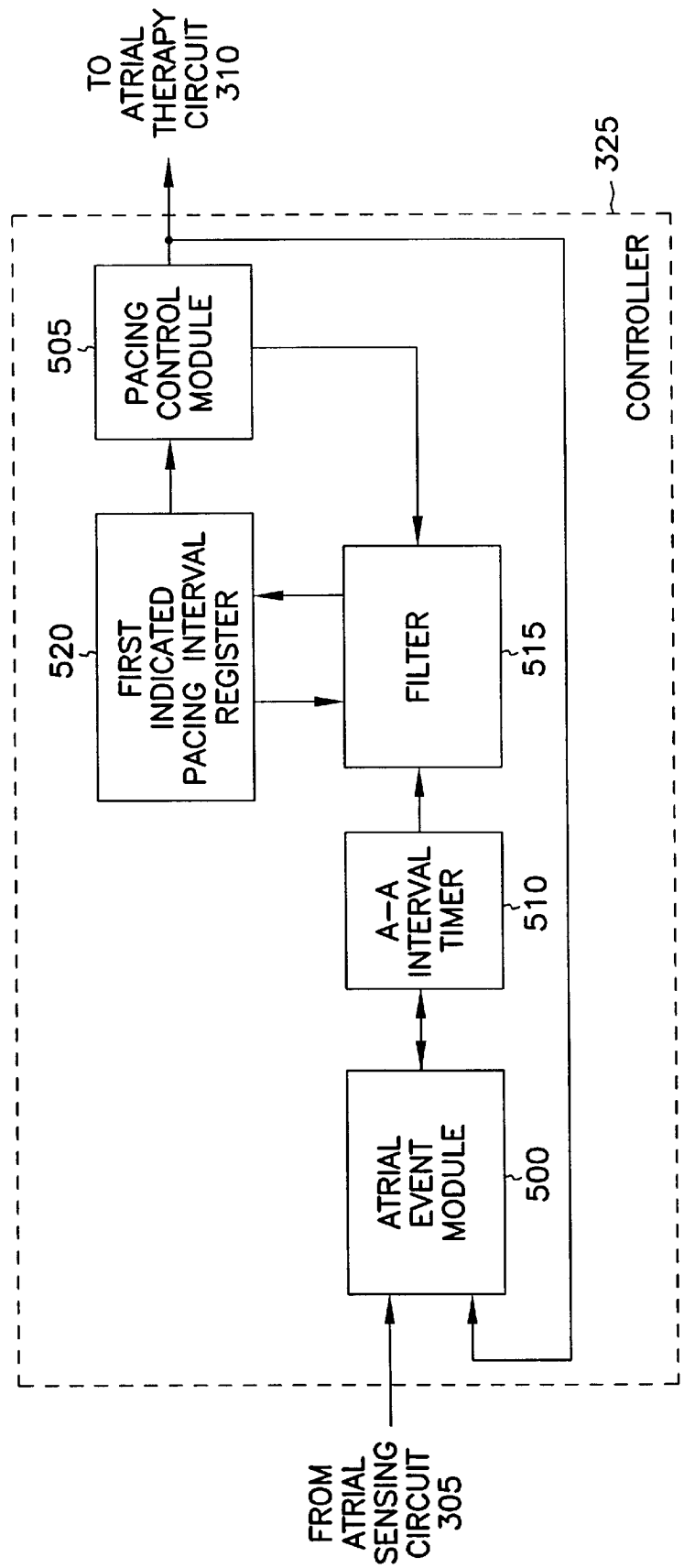
FIG. 5 is a schematic diagram illustrating generally one conceptualization of portions of a controller.

FIG. 5 is a schematic diagram illustrating generally, by way of example, but not by way of limitation, one conceptualization of portions of controller 325. At least one signal from atrial sensing circuit 305 is received by atrial event module 500, which recognizes the occurrence of atrial events included within the signal. Such events are also referred to as "beats," "activations," "depolarizations," "P-waves," or "contractions." Atrial event module 500 detects intrinsic events (also referred to as sensed events) from the signal obtained from atrial sensing circuit 305. Atrial event module 500 also detects evoked events (resulting from a pace) either from the signal obtained from atrial sensing circuit 305, or preferably from an atrial pacing control signal obtained from pacing control module 505, which also triggers the delivery of a pacing stimulus by atrial therapy circuit 310. Thus, atrial events include both intrinsic/sensed events and evoked/paced events.

A time interval between successive atrial events, referred to as an A-A interval, is recorded by a first timer, such as A-A interval timer 510. A filter 515 computes a "first indicated pacing interval," i.e., one indication of a desired time interval between atrial events or, stated differently, a desired atrial heart rate. The first indicated pacing interval is also referred to as an atrial pacing preference (APP) indicated pacing interval. In various embodiments, filter 515 includes an averager, a weighted averager, a median filter, an infinite impulse (IIR) filter, a finite impulse response (FIR) filter, or any other analog or digital signal processing circuit providing the desired signal processing described more particularly below.

In one embodiment, filter 515 computes a new value of the first indicated pacing interval (also referred to as the APP-indicated pacing interval) based on the duration of the most recent A-A interval recorded by timer 510 and on a previous value of the first indicated pacing interval stored in first indicated pacing interval register 520. Register 520 is then updated by storing the newly computed first indicated pacing interval in register 520. Based on the first indicated pacing interval stored in register 520, pacing control module 505 delivers control signals to atrial therapy circuit 310 for delivering therapy, such as pacing stimuli, at the APP-indicated atrial heart rate corresponding to the inverse of the duration of the first indicated pacing interval.

Filter Example 1

In general terms, for one embodiment, device 105 obtains A-A intervals between successive sensed or evoked atrial beats. Device 105 computes a new first indicated pacing interval based at least in part on the duration of the most recent A-A interval and a previous value of the first indicated pacing interval. Device 105 provides atrial pacing therapy delivered at a rate corresponding to the inverse of the duration of the first indicated pacing interval.

Figure 6:
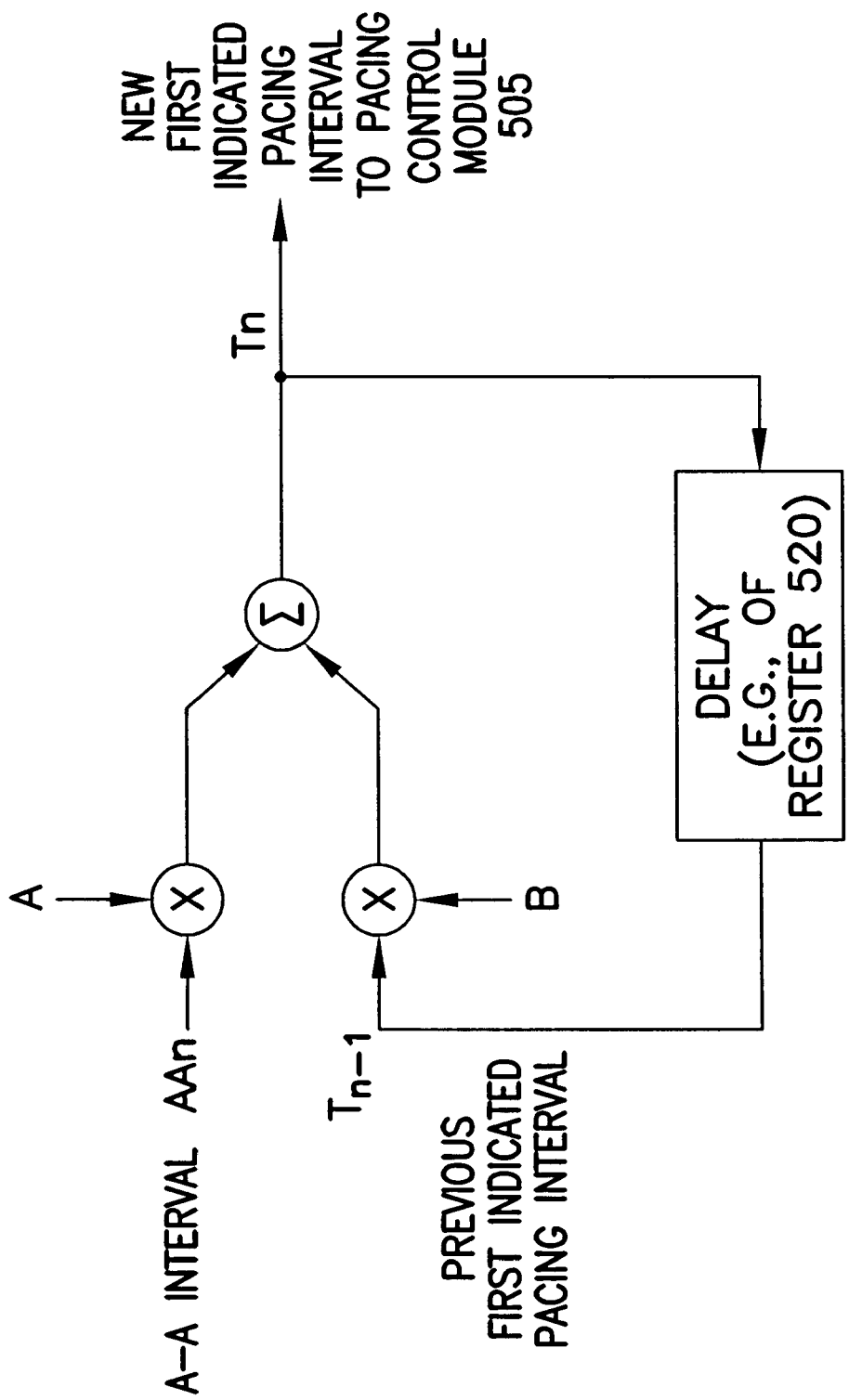
FIG. 6 is a signal flow diagram illustrating generally one embodiment of operating a filter.

FIG. 6 is a signal flow diagram illustrating generally, by way of example, but not by way of limitation, one embodiment of operating filter 515. Upon the occurrence of a sensed or evoked atrial beat, timer 510 provides filter 515 with the duration of the A-A interval concluded by that beat, which is referred to as the most recent A-A interval ($AA_n$). Filter 515 also receives the previous value of the first indicated pacing interval ($T_{n-1}$) stored in register 520. The most recent A-A interval $AA_n$ and the previous value of the first indicated pacing interval $T_{n-1}$ are each scaled by respective constants A and B, and then summed to obtain a new value of the first indicated pacing interval ($T_n$), which is stored in register 520 and provided to pacing control module 505. In one embodiment, the coefficients A and B are different values, and are either programmable, variable, or constant.

If no atrial beat is sensed during the new first indicated pacing interval $T_n$, which is measured as the time from the occurrence of the atrial beat concluding the most recent A-A interval $AA_n$, then pacing control module 505 instructs atrial therapy circuit 310 to deliver an atrial pacing pulse upon the expiration of the new first indicated pacing interval $T_n$. In one embodiment, operation of the filter is described by $T_n = A \cdot AA_n + B \cdot T_{n-1}$, where A and B are coefficients (also referred to as "weights"), $AA_n$ is the most recent A-A interval duration, and $T_{n-1}$ is the previous value of the first indicated pacing interval.

Initialization of filter 515 includes seeding the filter by storing, in register 520, an initial interval value. In one embodiment, register 520 is initialized to an interval value corresponding to a lower rate limit (LRL), i.e., a minimum rate at which pacing pulses are delivered by device 105. Register 520 could alternatively be initialized with any other suitable value.

Filter Example 2

In one embodiment, operation of filter 515 is based on whether the beat concluding the most recent A-A interval $AA_n$ is a sensed/intrinsic beat or a paced/evoked beat. In this embodiment, the pacing control module 505, which controls the timing and delivery of pacing pulses, provides an input to filter 515 that indicates whether the most recent A-A interval $AA_n$ was concluded by an evoked beat initiated by a pacing stimulus delivered by device 105, or was concluded by an intrinsic beat sensed by atrial sensing circuit 305.

In general terms, if the most recent A-A interval $AA_n$ is concluded by a sensed/intrinsic beat, then filter 515 provides a new first indicated pacing interval $T_n$ that is adjusted from the value of the previous first indicated pacing interval $T_{n-1}$ such as, for example, decreased by an amount that is based at least partially on the duration of the most recent A-A interval $AA_n$ and on the duration of the previous value of the first indicated pacing interval $T_{n-1}$. If, however, the most recent A-A interval $AA_n$ is concluded by a paced/evoked beat, then filter 515 provides a new first indicated pacing interval $T_n$ that is increased from the value of the previous first indicated pacing interval $T_{n-1}$, such as, for example, by an amount that is based at least partially on the duration of the most recent A-A interval $AA_n$ and on the duration of the previous value of the first indicated pacing interval $T_{n-1}$. If no atrial beat is sensed during the new first indicated pacing interval $T_n$, which is measured as the time from the occurrence of the atrial beat concluding the most recent A-A interval $AA_n$, then pacing control module 505 instructs atrial therapy circuit 310 to deliver an atrial pacing pulse upon the expiration of the new first indicated pacing interval $T_n$.

Figure 7:
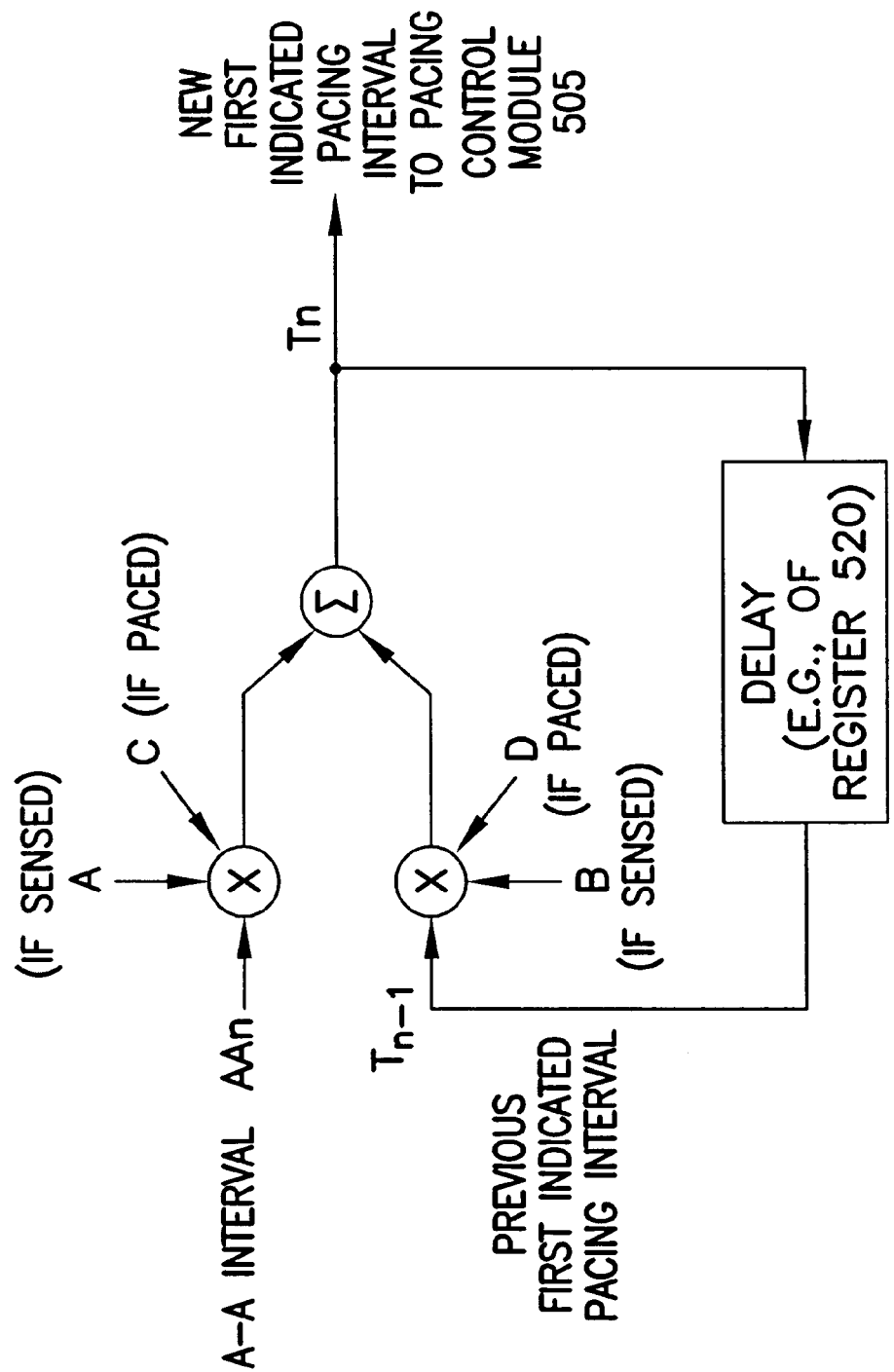
FIG. 7 is a signal flow diagram illustrating generally aspects of another conceptualization of operating the filter.

FIG. 7 is a signal flow diagram, illustrating generally, by way of example, but not by way of limitation, another conceptualization of operating filter 515, with certain differences from FIG. 6 more particularly described below. In this embodiment, the pacing control module 505, which controls the timing and delivery of pacing pulses, provides an input to filter 515 that indicates whether the most recent A-A interval $AA_n$ was concluded by an evoked beat initiated by a pacing stimulus delivered by device 105, or was concluded by an intrinsic beat sensed by a trial sensing circuit 305.

If the most recent A-A interval $AA_n$ was concluded by an intrinsic beat, then the most recent A-A interval, $AA_n$, and the previous value of the first indicated pacing interval, $T_{n-1}$, are each scaled by respective constants A and B, and then summed to obtain the new value of the first indicated pacing interval $T_n$, which is stored in register 520 and provided to pacing control module 505. Alternatively, if the most recent A-A interval $AA_n$ was concluded by an evoked/paced beat, then the most recent A-A interval $AA_n$ and the previous value of the first indicated pacing interval $T_{n-1}$ are each scaled by respective constants C and D, and then summed to obtain the new value of the first indicated pacing interval $T_n$, which is stored in register 520 and provided to pacing control module 505. In one embodiment, the coefficients C and D are different from each other, and are either programmable, variable, or constant. In a further embodiment, the coefficient C is a different value from the coefficient A, and/or the coefficient D is a different value than the coefficient B, and these coefficients are either programmable, variable, or constant. In another embodiment, the coefficient D is the same value as the coefficient B.

In one embodiment, operation of filter 515 is described by $T_n = A \cdot AA_n + B \cdot T_{n-1}$, if $AA_n$ is concluded by an intrinsic beat, and is described by $T_n = C \cdot AA_n + D \cdot T_{n-1}$, if $AA_n$ is concluded by a paced beat, where A, B, C and D are coefficients (also referred to as "weights"), $AA_n$ is the most recent A-A interval duration, $T_n$ is the new value of the first indicated pacing interval, and $T_{n-1}$ is the previous value of the first indicated pacing interval. If no atrial beat is sensed during the new first indicated pacing interval $T_n$, which is measured as the time from the occurrence of the atrial beat concluding the most recent A-A interval $AA_n$, then pacing control module 505 instructs atrial therapy circuit 310 to deliver an atrial pacing pulse upon the expiration of the new first indicated pacing interval $T_n$.

Filter Example 3

Figure 8:
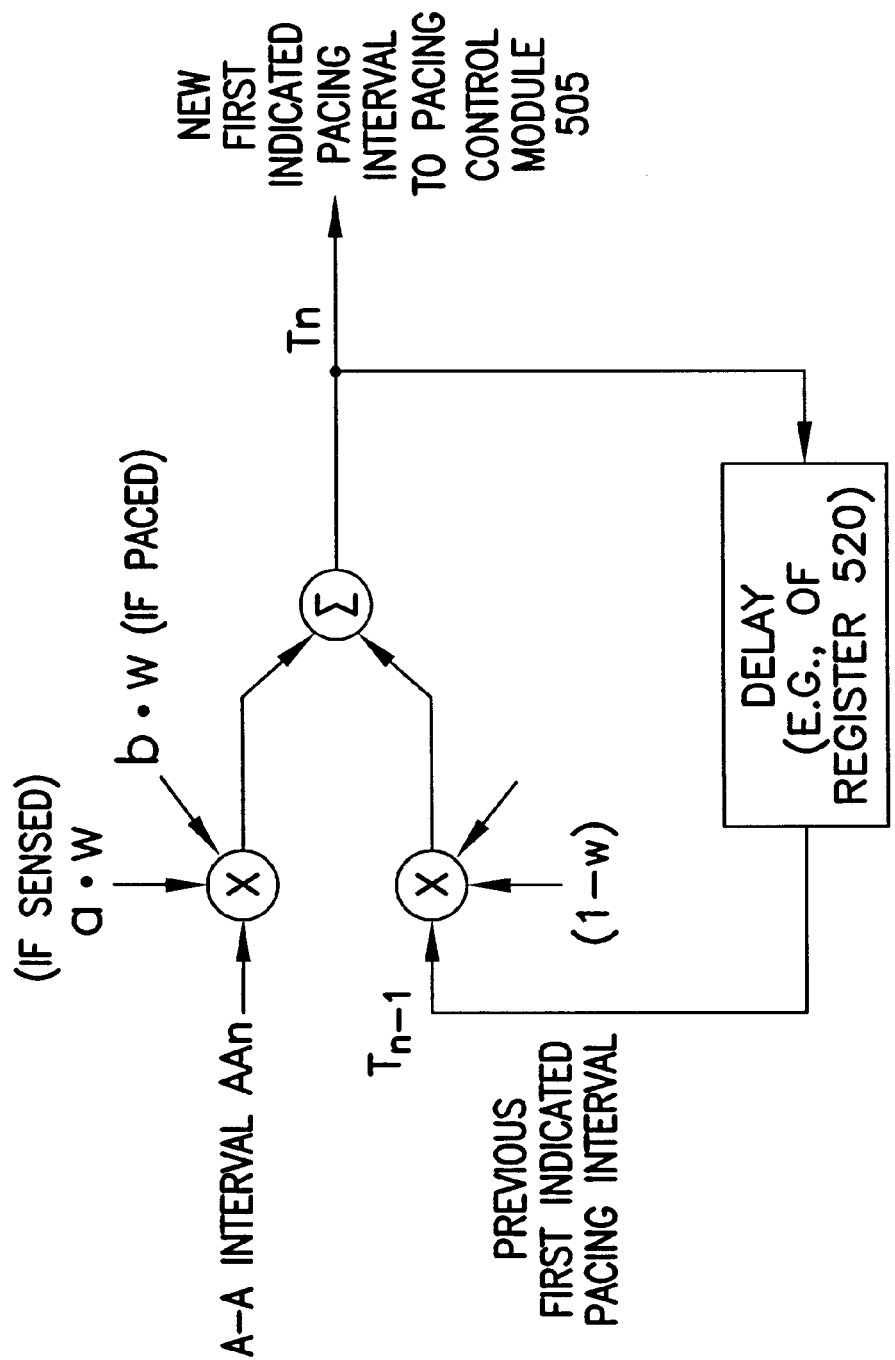
FIG. 8 is a signal flow diagram illustrating generally aspects of a further conceptualization of operating the filter.

In another embodiment, these coefficients can be more particularly described using an intrinsic coefficient (a), a paced coefficient (b), and a weighting coefficient (w). In one such embodiment, $A = a \cdot w$, $B = (1-w)$, $C = b \cdot w$, and $D = (1-w)$. In one example, operation of the filter 515 is described by $T_n = a \cdot w \cdot AA_n 30 \; (1-w) \cdot T_{n-1}$, if $AA_n$ is concluded by an intrinsic beat, otherwise is described by $T_n = b \cdot w \cdot AA_n + (1-w) \cdot T_{n-1}$, if $AA_n$ is concluded by a paced beat, as illustrated generally, by way of example, but not by way of limitation, in the signal flow graph of FIG. 8. If no atrial beat is sensed during the new first indicated pacing interval $T_n$, which is measured as the time from the occurrence of the atrial beat concluding the most recent A-A interval $AA_n$, then pacing control module 505 instructs atrial therapy circuit 310 to deliver an atrial pacing pulse upon the expiration of the new first indicated pacing interval $T_n$. In one embodiment, the coefficients a and b are different from each other, and are either programmable, variable, or constant.

The above-described parameters (e.g., A, B, C, D, a, b, w) are stated in terms of time intervals (e.g., $AA_n$, $T_n$, $T_{n-1}$). However, an alternate system may produce results in terms of rate, rather than time intervals, without departing from the present method and apparatus. In one embodiment, weighting coefficient w, intrinsic coefficient a, and paced coefficient b, are variables. Different selections of w, a, and b, will result in different operation of the present method and apparatus. For example, as w increases the weighting effect of the most recent A-A interval $AA_n$ increases and the weighting effect of the previous first indicated pacing rate $T_{n-1}$ decreases. In one embodiment, $w = 1/16 = 0.0625$. In another embodiment, $w = 1/32$. Another possible range for w is from $w = 1/2$ to $w = 1/1024$. A further possible range for w is from $w \sim 0$ to $w \sim 1$. Other values of w, which need not include division by powers of two, may be substituted without departing from the present method and apparatus.

In one embodiment, intrinsic coefficient a, is selected to be less than (or, alternatively, less than or equal to) 1.0. In one example, the intrinsic coefficient a is selected to be lesser in value than the pacing coefficient b. In one embodiment, $a \sim 0.6$ and $b \sim 1.5$. In another embodiment, $a = 1.0$ and $b = 1.05$. One possible range for a is from $a = 0.6$ to $a = 1.0$, and for b is from $b = 1.05$ to $b = 1.5$. The coefficients may vary without departing from the present method and apparatus.

In one embodiment, for $a < 1.0$ filter 515 provides a new first indicated pacing interval $T_n$ that is at least slightly shorter than the expected intrinsic A-A interval being measured by timer 515. Thus, filter 515 operates to promote atrial pacing by increasing the APP-indicated rate until it becomes slightly faster than the intrinsic atrial rate. The APP-indicated rate is then gradually decreased to search for the underlying intrinsic atrial heart rate. After a sensed atrial beat, the APP filter 515 again increases the APP indicated pacing rate until it becomes faster than the intrinsic atrial rate by a small amount. As a result, most atrial heart beats are paced, rather than sensed. This decreases the likelihood of the occurrence of an atrial tachyarrhythmia, such as atrial fibrillation. The decreased likelihood of atrial tachyarrhythmia, in turn, decreases the likelihood of inducing a ventricular arrhythmia, either as a result of the atrial tachyarrhythmia, or as the result of delivering a defibrillation shock to treat the atrial tachyarrhythmia.

Controller Example 2

Figure 9:
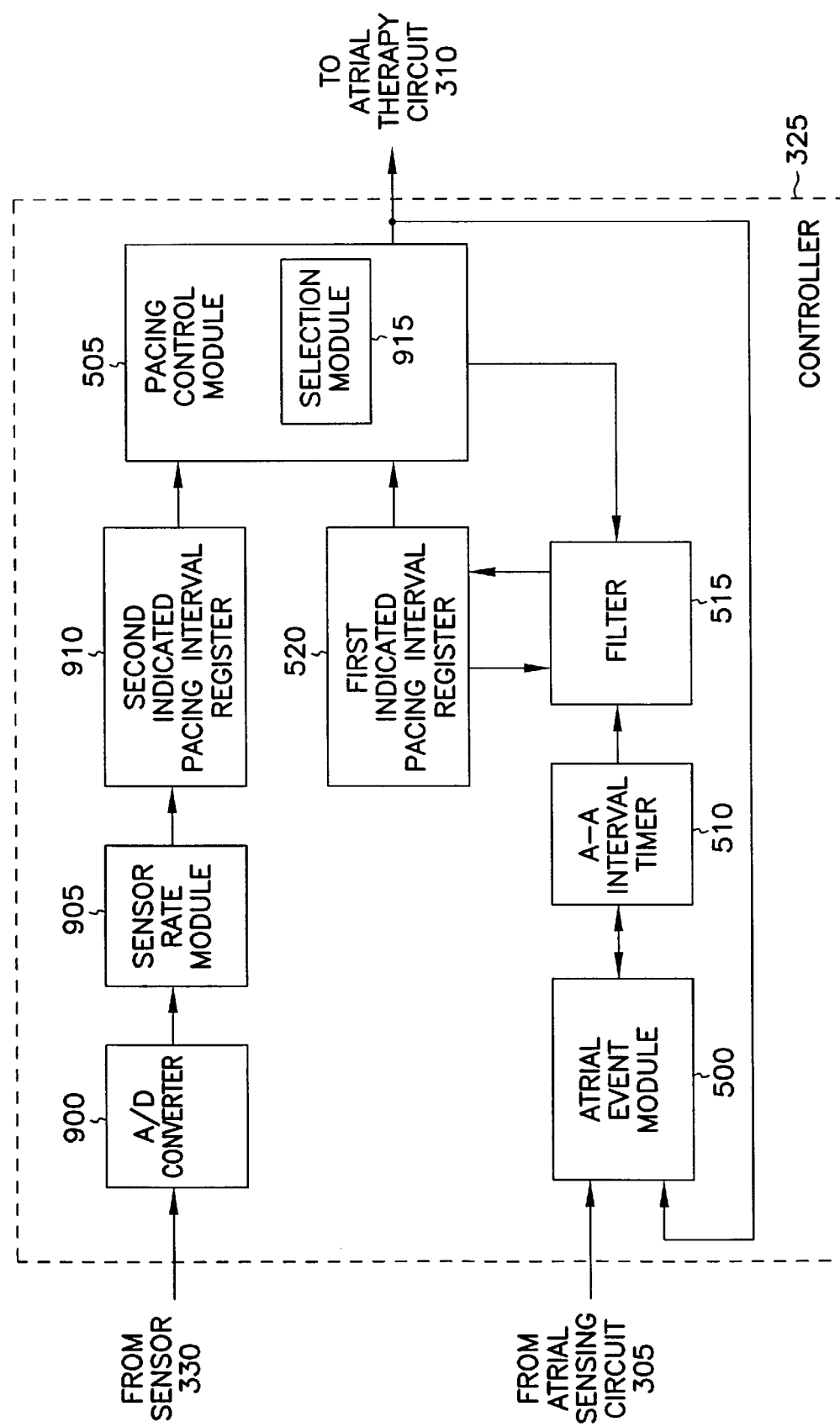
FIG. 9 is a schematic diagram illustrating generally another conceptualization of portions of a controller.

FIG. 9 is a schematic diagram illustrating generally, by way of example, but not by way of limitation, another conceptualization of portions of controller 325, with certain differences from FIG. 5 more particularly described below. In FIG. 9, controller 325 receives from sensor 330 a signal including information from which a physiologically desired heart rate (e.g., based on the patient's activity, respiration, or any other suitable indicator of metabolic need) can be derived. The sensor signal is digitized by an A/D converter 900. The digitized signal is processed by a sensor rate module 905, which computes a desired heart rate that is expressed in terms of a second indicated pacing interval stored in register 910. The second indicated pacing interval is also referred to as a sensor-indicated pacing interval, or if expressed in terms of rate, a sensor-indicated pacing rate.

Pacing control module 505 delivers a control signal, which directs atrial therapy circuit 310 to deliver a pacing pulse, based on either (or both) of the first or second indicated pacing intervals, stored in registers 520 and 910, respectively. In one embodiment, pacing control module 505 includes a selection module 915 that selects between the new first indicated pacing interval $T_n$ and the sensor-based second indicated pacing interval.

In one embodiment, selection module 915 selects the shorter of the first and second indicated pacing intervals as the selected indicated pacing interval $S_n$. If no atrial beat is sensed during the selected indicated pacing interval $S_n$, which is measured as the time from the occurrence of the atrial beat concluding the most recent A-A interval $AA_n$, then pacing control module 505 instructs atrial therapy circuit 320 to deliver an atrial pacing pulse upon the expiration of the selected indicated pacing interval $S_n$.

In general terms, for this embodiment, the atrium is paced at the higher of the sensor indicated rate and the APP-indicated rate. If, for example, the patient is resting, such that the sensor indicated rate is lower than the patient's intrinsic rate, then atrial pacing pulses will be delivered at the APP-indicated rate, which is typically slightly higher than the patient's intrinsic atrial heart rate. But if, for example, the patient is active, such that the sensor indicated rate is higher than the APP-indicated rate, then pacing pulses generally will be delivered at the sensor indicated rate. In an alternative embodiment, the pacing rate is determined by blending the sensor indicated rate and the APP-indicated rate, rather than by selecting the higher of these two indicated rates (i.e., the shorter of the first and second indicated pacing intervals). In one such example, selection module 915 applies predetermined or other weights to the first and second indicated pacing intervals to compute the selected pacing interval $S_n$.

Filter Rate Behavior Example 1

Figure 10:
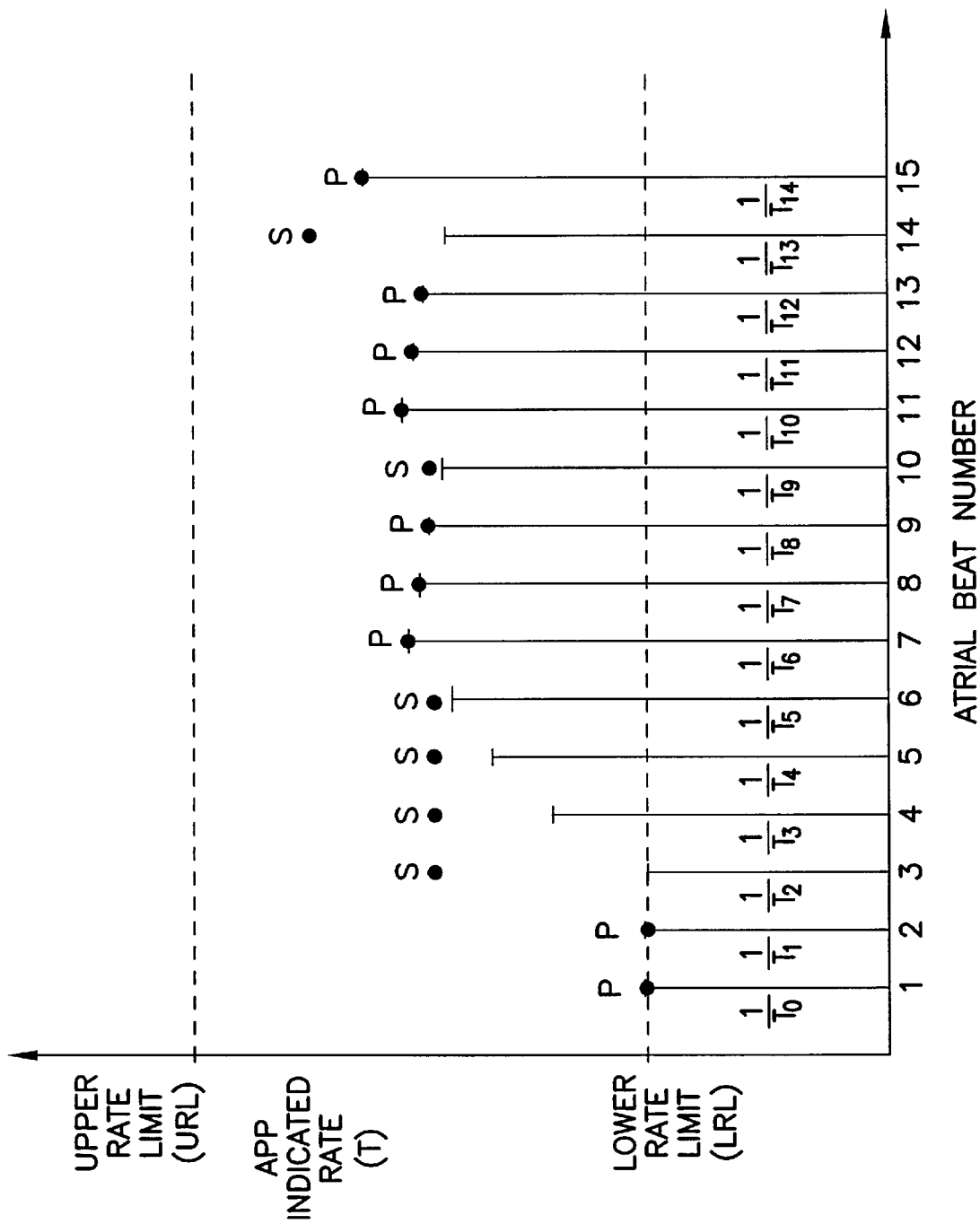
FIG. 10 is a graph illustrating generally one embodiment of operating a filter to provide a first indicated rate, such as an Atrial Pacing Preference ("APP") indicated rate, for successive atrial heart beats.

FIG. 10 is a graph illustrating generally, by way of example, but not by way of limitation, one embodiment of an APP-indicated rate for successive atrial heart beats for one mode of operating filter 515. As discussed above, the APP-indicated rate is simply the frequency, between atrial heart beats, associated with the first indicated pacing interval. Stated differently, the APP indicated rate is inversely related to the duration of the first indicated pacing interval. If pacing is based solely on the APP indicated rate, pacing control module 505 directs atrial therapy circuit 310 to issue a pacing pulse after the time since the last atrial beat equals or exceeds the first indicated pacing interval. However, as described above, in certain embodiments, pacing control module 505 directs atrial therapy circuit 310 to issue a pacing pulse based on factors other than the APP indicated rate such as for, example, based on the sensor indicated rate.

In the example illustrated in FIG. 10, a first paced atrial beat, indicated by a "P" was issued upon expiration of the first indicated pacing interval (i.e., the APP indicated pacing interval) $T_0$, as computed based on a previous atrial beat. In one embodiment, the new APP indicated pacing interval $T_1$ is computed based on the duration of most recent A-A interval $AA_1$ and a previous value of the APP indicated pacing interval $T_0$, as discussed above. In FIG. 10, the new APP indicated pacing interval $T_1$ corresponds to a lower rate limit (LRL) time interval. In one embodiment, as illustrated in FIG. 10, the allowable range of the APP indicated pacing interval is limited so that the APP indicated pacing interval does not exceed the duration of the LRL time interval, and so that the APP indicated pacing interval is not shorter than the duration of an upper rate limit (URL) time interval.

In the example of FIG. 10, the second atrial beat is also paced upon expiration of the APP indicated pacing interval $T_1$. In one embodiment, the new APP indicated pacing interval $T_2$ is computed based on the duration of most recent A-A interval $AA_2$ and a previous value of the APP indicated pacing interval, $T_1$, as discussed above. The first and second atrial beats are paced beats because the APP indicated atrial heart rate is higher than the underlying intrinsic atrial heart rate.

The third atrial beat is sensed well before expiration of the APP indicated pacing interval $T_2$, such that no pacing pulse is issued. For the sensed third atrial beat, filter 515 computes the new APP indicated pacing interval $T_3$ as being shorter in duration relative to the previous APP indicated pacing interval $T_2$.

The fourth, fifth, and sixth atrial beats are sensed before expiration of the APP indicated pacing interval $T_3$, $T_4$, and $T_5$, respectively. For each of the sensed fourth, fifth, and sixth atrial beats, filter 515 computes a new APP indicated pacing interval as being shorter in duration relative to the previous APP indicated pacing interval.

At the time of the seventh atrial beat, the APP indicated heart rate has increased above the underlying intrinsic atrial heart rate, such that the seventh atrial beat is paced upon expiration of the APP indicated pacing interval $T_6$. Because the seventh atrial beat is paced, rather than sensed, the new APP indicated pacing interval $T_7$ is computed as being longer than the previous APP indicated pacing interval $T_6$.

Similarly, the eighth and ninth atrial beats are each paced upon expiration of the corresponding APP indicated pacing interval, i.e., $T_7$, and $T_8$, respectively. Each APP indicated pacing interval $T_7$, and $T_8$ is longer than the corresponding previous APP indicated pacing interval, i.e., $T_6$, and $T_7$, respectively. In this way, the APP indicated atrial heart rate is gradually decreased to search for the underlying intrinsic atrial heart rate.

At the time of the tenth atrial beat, the APP indicated heart rate has been lowered sufficiently to allow the sensing of the tenth atrial beat. The tenth atrial beat is sensed before expiration of the APP indicated pacing interval $T_9$, such that no pacing pulse is issued. For the sensed tenth atrial beat, filter 515 computes the new APP indicated pacing interval $T_{10}$ as being shorter in duration relative to the previous APP indicated pacing interval $T_9$.

The eleventh atrial beat is paced upon expiration of the APP indicated pacing interval $T_{10}$. For the paced eleventh atrial beat, filter 515 computes the new APP indicated pacing interval $T_{11}$ as being longer in duration relative to the previous APP indicated pacing interval $T_{10}$. Similarly, the twelfth and thirteenth atrial beats are each paced upon expiration of the corresponding APP indicated pacing interval, i.e., $T_{11}$, and $T_{12}$, respectively. Each APP indicated pacing interval $T_{12}$, and $T_{13}$ is longer than the corresponding previous APP indicated pacing interval, i.e., $T_{11}$, and $T_{12}$, respectively. In this way, the APP indicated atrial heart rate is gradually decreased to find the underlying intrinsic atrial heart rate.

The fourteenth atrial beat is sensed before expiration of the APP indicated pacing interval $T_{13}$, such that no pacing pulse is issued. For the sensed fourteenth atrial beat, filter 515 computes the new APP indicated pacing interval $T_{14}$ as being shorter in duration relative to the previous APP indicated pacing interval $T_{13}$.

The fifteenth atrial beat is paced upon expiration of the APP indicated pacing interval $T_{14}$. For the paced fifteenth atrial beat, filter 515 computes the new APP indicated pacing interval $T_{15}$ as being longer in duration relative to the previous APP indicated pacing interval $T_{14}$.

The intrinsic coefficient a of filter 515 controls the "attack slope" of the APP indicated heart rate as the APP indicated heart rate increases because of sensed intrinsic beats. The paced coefficient b of filter 515 controls the "decay slope" of the APP indicated heart rate as the APP indicated heart rate decreases during periods of paced beats. In one embodiment, in which a<1.0 and b>1.0, decreasing the value of a further beneath 1.0 increases the attack slope such that the APP indicated rate increases faster in response to sensed intrinsic beats, while decreasing the value of b toward 1.0 decreases the decay slope such that the APP indicated rate decreases more slowly during periods of paced beats. Conversely, for a<1.0 and b>1.0, increasing the value of a toward 1.0 decreases the attack slope such that the APP indicated rate increases more slowly in response to sensed intrinsic beats, while increasing the value of b from 1.0 increases the decay slope such that the APP indicated rate decreases more quickly during periods of paced beats.

In one embodiment, for a<1.0 and b>1.0, decreasing both a and b increases the APP indicated rate such that the APP indicated rate is higher above the mean intrinsic rate. Because the APP indicated rate is higher, variability in the intrinsic heart rate is less likely to result in sensed events. On the other hand, for a<1.0 and b>1.0, increasing both a and b decreases the APP indicated rate such that it is closer to, the mean intrinsic rate. Because the APP indicated rate is closer to the mean intrinsic rate, the same degree of variability in the intrinsic heart rate is more likely to result in sensed events. Thus, by optimizing the coefficients of filter 515, as discussed above, it is possible to obtain more intrinsic beats than paced beats for a particular degree of variability in the patient's heart rate. In one embodiment, these coefficients are programmable by the user, such as by using remote programmer 125. In another embodiment, the user selects a desired performance parameter (e.g., desired degree of overdrive pacing, desired attack slope, desired decay slope, etc.) from a corresponding range of possible values, and device 105 automatically selects the appropriate combination of coefficients of filter 515 to provide a filter setting that corresponds to the selected user-programmed performance parameter, as illustrated generally by Table 1. Other levels of programmability or different combinations of coefficients may also be used.

TABLE 1

Example of Automatic Selection of Aspects of Filter Setting Based on a User-Programmable Performance Parameter.

| User-Programmable Performance Parameter | Intrinsic Coefficient a | Paced Coefficient b |
|---|---|---|
| 1 (Less Aggressive Attack/Decay) | 1.0 | 1.05 |
| 2 | 0.9 | 1.2 |
| 3 | 0.8 | 1.3 |
| 4 | 0.7 | 1.4 |
| 5 (More Aggressive Attack/Decay) | 0.6 | 1.5 |

FIG. 10 illustrates that sensed atrial beats increase the APP indicated rate by an amount that is based on the sensed atrial heart rate. Thus, for an abrupt and large increase in sensed atrial rate, the APP indicated rate will increase faster than for a slower and smaller increase in sensed atrial heart rate. However, increases in the APP indicated rate do not depend solely on the sensed atrial heart rate. Instead, such increases in the APP indicated heart rate also depend on the previous value of the APP indicated heart rate. This provides a smoothing function so that the APP indicated heart rate is not overly sensitive to a single extremely premature atrial beat, changes in the atrial rate are more gradual, and the degree of such rate changes is programmably adjustable, as described above. Moreover, in one embodiment, filter 515 operates continuously to provide continuous rate adjustment based on the APP indicated rate.

Filter Rate Behavior Example 2

Figure 11:
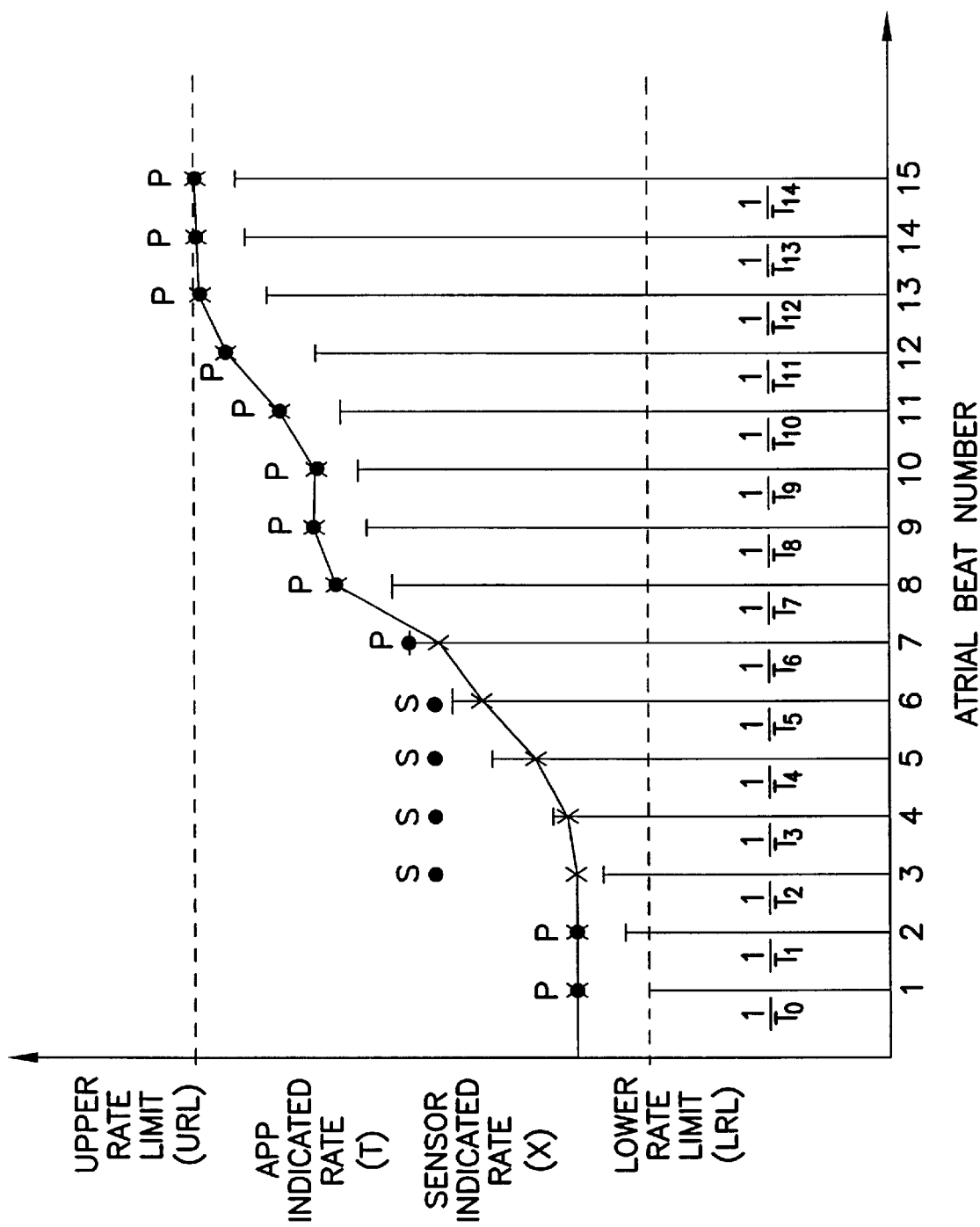
FIG. 11 is a graph illustrating generally another embodiment of operating a filter to provide a first indicated pacing rate, such as an APP indicated rate, and delivering therapy based on the first indicated pacing rate and based on a second indicated pacing rate, such as a sensor indicated rate.

FIG. 11 is a graph illustrating generally, by way of example, but not by way of limitation, one embodiment of selecting between more than one indicated pacing interval. FIG. 11 is similar to FIG. 10 in some respects, but FIG. 11 includes a second indicated pacing interval. In one embodiment, the first indicated pacing interval is the APP indicated pacing interval, described above, and the second indicated pacing interval is a sensor indicated pacing interval, from an accelerometer, minute ventilation, or other indication of the patient's physiological need for increased cardiac output.

In one embodiment, a selected indicated pacing interval is based on the shorter of the first and second indicated pacing intervals. Stated differently, device 105 provides pacing pulses at the higher indicated pacing rate. In the example illustrated in FIG. 11, the first and second beats and the eighth through fifteenth beats are paced at the sensor indicated rate, because it is higher than the APP indicated atrial rate and the intrinsic (sensed) atrial rate. The third, fourth, fifth and sixth atrial beats are sensed intrinsic beats that are sensed during the shorter of either of the APP and sensor indicated pacing intervals. The seventh beat is paced at the APP indicated rate, because it is higher than the sensor indicated rate, and because no intrinsic beat is sensed during the APP indicated interval $T_6$. In this embodiment, the ranges of both the sensor indicated rate and the APP indicated rate are limited so that they do not extend to rates higher than the URL or to rates lower than the LRL. In one embodiment, the above-described equations for filter 515 operate to increase the APP indicated rate toward the sensor-indicated rate when the sensor indicated rate is greater than the APP indicated rate, as illustrated by first through third and eighth through fifteenth beats in FIG. 11. In an alternate embodiment, however, $T_n = b \cdot w \cdot AA_n + (1-w) \cdot T_{n-1}$, if $AA_n$ is concluded by a APP indicated paced beat, and $T_n = T_{n-1}$ if $AA_n$ is concluded by a sensor indicated paced beat, thereby leaving the APP indicated rate unchanged for sensor indicated paced beats. In one embodiment, the LRL and the URL are programmable by the user, such as by using remote programmer 125.

Filter Example 3

In one embodiment, filter 515 includes variable coefficients such as, for example, coefficients that are a function of heart rate (or its corresponding time interval). In one example, operation of the filter 515 is described by $T_n = a \cdot w \cdot AA_n + (1-w) \cdot T_{n-1}$, if $AA_n$ is concluded by an intrinsic beat, otherwise is described by $T_n = b \cdot w \cdot AA_n + (1-w) \cdot T_{n-1}$, if $AA_n$ is concluded by a paced beat, where at least one of a and b are linear, piecewise linear, or nonlinear functions of one or more previous A-A intervals such as, for example, the most recent A-A interval, $AA_n$.

Figure 12:
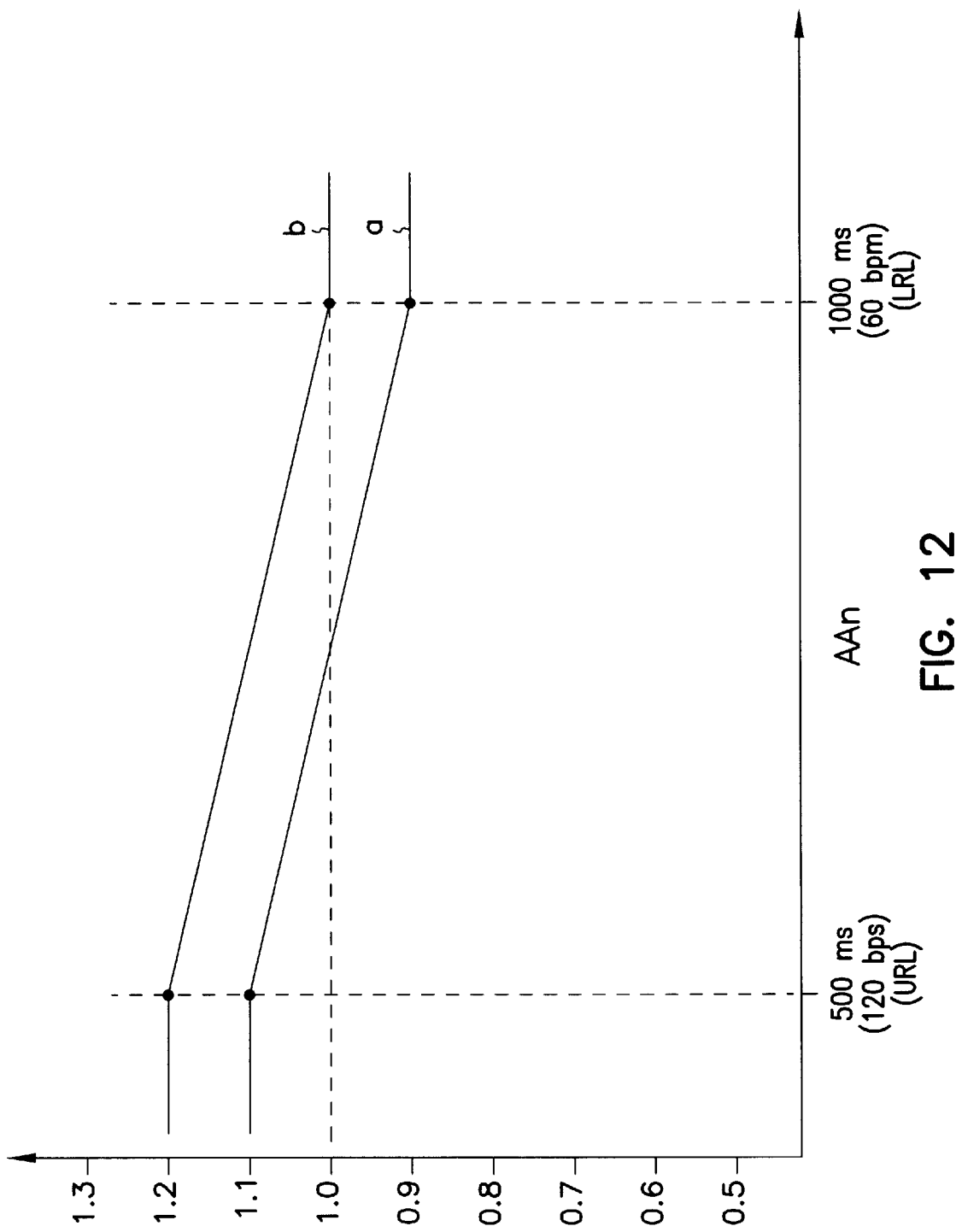
FIG. 12 is a graph illustrating generally one embodiment of using at least one of coefficients a and b as a function of heart rate (or a corresponding time interval).

FIG. 12 is a graph illustrating generally, by way of example, but not by way of limitation, one embodiment of using at least one of coefficients a and b as a function of one or more previous A-A intervals such as, for example, the most recent A-A interval, $AA_n$. In one such example, a is less than 1.0 when $AA_n$ is at or near the lower rate limit (e.g., 1000 millisecond interval or 60 beats/minute), and a is greater than 1.0 when $AA_n$ is at or near the upper rate limit (e.g., 500 millisecond interval or 120 beats/minute). For a constant b, using a smaller value of a at lower rates will increase the pacing rate more quickly for sensed events; using a larger value of a at higher rates increases the pacing rate more slowly for sensed events. In another example, b is close to 1.0 when $AA_n$ is at or near the lower rate limit, and b is greater than 1.0 when $AA_n$ is at or near the upper rate limit. For a constant a, using a smaller value of b at lower rates will decrease the pacing rate more slowly for paced events; using a larger value of b at higher rates decreases pacing rate more quickly for paced events.

Conclusion

The above-described system provides, among other things, a cardiac rhythm management system including an atrial pacing preference (APP) filter for promoting atrial pacing. The APP filter controls the timing of delivery of atrial pacing pulses. The atrial pacing pulses are delivered at a first indicated pacing rate, i.e., the APP-indicated rate, that is typically at a small amount above the intrinsic atrial heart rate. For sensed beats, the APP indicated pacing rate is increased until it becomes slightly faster than the intrinsic atrial heart rate. The APP-indicated pacing rate is then gradually decreased to search for the underlying intrinsic atrial heart rate. Then, after a sensed atrial beat, the APP filter again increases the APP indicated pacing rate until it becomes faster than the intrinsic atrial rate by a small amount. As a result, most atrial heart beats are paced, rather than sensed. This decreases the likelihood of the occurrence of an atrial tachyarrhythmia, such as atrial fibrillation. The decreased likelihood of atrial tachyarrhythmia, in turn, decreases the likelihood of inducing a ventricular arrhythmia, either as a result of the atrial tachyarrhythmia, or as the result of delivering a defibrillation shock to treat the atrial tachyarrhythmia.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method, including:
   obtaining A-A intervals between atrial beats;
   computing a first indicated pacing interval based at least on a most recent A-A interval duration and a previous value of the first indicated pacing interval; and
   providing atrial pacing therapy at a rate that generally exceeds an intrinsic atrial heart rate, based on the first indicated pacing interval.

2. The method of claim 1, in which computing the first indicated pacing interval includes differently weighting at least one of (1) the most recent A-A interval duration, or (2) the previous value of the first indicated pacing interval, if the most-recent A-A interval is concluded by a paced beat than if the most recent A-A interval is concluded by a sensed beat.

3. The method of claim 1, in which computing the first indicated pacing interval includes summing a first addend based on the most recent A-A interval duration and a second addend based on the previous value of the first indicated pacing interval, wherein at least one of the first and second addends is different if the most recent A-A interval is concluded by an intrinsic beat than if the most recent A-A interval is concluded by a paced beat.

4. The method of claim 1, in which computing the first indicated pacing interval $(T_n)$ is carried out according to $T_n = A \cdot AA_n + B \cdot T_{n-1}$, where A and B are coefficients, $AA_n$ is the most recent A-A interval duration, and $T_{n-1}$ is the previous value of the first indicated pacing interval.

5. The method of claim 4, in which A and B are different values.

6. The method of claim 4, in which computing the first indicated pacing interval $(T_n)$ is carried out according to: $T_n = A \cdot AA_n + B \cdot T_{n-1}$, if $AA_n$ is concluded by an intrinsic beat, otherwise is carried out according to $T_n = C \cdot AA_n + D \cdot T_{n-1}$, if $AA_n$ is concluded by a paced beat, where C and D are coefficients.

7. The method of claim 6, in which C and D are different values.

8. The method of claim 7, in which C and A are different values.

9. The method of claim 6, in which at least one of A, B, C, and D is a function of heart rate.

10. The method of claim 1, in which computing the first indicated pacing interval $(T_n)$ is carried out according to $T_n = a \cdot w \cdot AA_n + (1-w) \cdot T_{n-1}$, where a and w are coefficients, $AA_n$ is the most recent A-A interval duration, and $T_{n-1}$ is the previous value of the first indicated pacing interval.

11. The method of claim 10, in which a is greater than a value selected from the group consisting of 0.5 and 1.0.

12. The method of claim 11, in which a is approximately equal to 1.1.

13. The method of claim 10, in which computing the first indicated pacing interval $(T_n)$ is carried out according to: $T_n = a \cdot w \cdot AA_n + (1-w) \cdot T_{n-1}$, if $AA_n$ is concluded by an intrinsic beat, otherwise is carried out according to $T_n = b \cdot w \cdot AA_n + (1-w) \cdot T_{n-1}$, if $AA_n$ is concluded by a paced beat, where b is a coefficient.

14. The method of claim 13, in which a and b are different values.

15. The method of claim 14, in which a is greater than a value selected from the group consisting of 0.5 and 1.0.

16. The method of claim 15, in which b is greater than a.

17. The method of claim 14, in which b is greater than a.

18. The method of claim 14, in which a is approximately equal to 1.1 and b is approximately equal to 1.2.

19. The method of claim 13, in which at least one of a, b, and w are a function of heart rate.

20. The method of claim 10, in which w is approximately between 0 and 1.

21. The method of claim 1, in which providing pacing therapy is also based on a second indicated pacing interval that is based on a sensor.

22. The method of claim 21, in which providing pacing therapy is based on the shorter of the first and second indicated pacing intervals.

23. The method of claim 22, in which the first and second indicated pacing intervals do not fall outside a range bounded by intervals corresponding to upper and lower rate limits.

24. The method of claim 1, in which computing the first indicated pacing interval includes limiting the minimum first indicated pacing interval to be longer than or equal to an interval corresponding to an upper rate limit.

25. The method of claim 1, in which computing the first indicated pacing interval includes limiting the maximum first indicated pacing interval to be shorter than or equal to an interval corresponding to a lower rate limit.

26. A cardiac rhythm management system, including:
    an atrial sensing circuit for sensing atrial beats;
    a controller, obtaining A-A intervals between atrial beats and computing a first indicated pacing interval based at least on a most recent A-A interval duration and a previous value of the first indicated pacing interval; and
    an atrial therapy circuit, providing pacing therapy, at a rate that generally exceeds an intrinsic atrial heart rate, based on the first indicated pacing interval.

27. The system of claim 26, in which the controller adjusts the first indicated pacing interval, by differently weighting at least one of (1) the most recent A-A interval duration, or (2) the previous value of the first indicated pacing interval, if the most-recent A-A interval is concluded by a paced beat than if the most recent A-A interval is concluded by a sensed beat.

28. The system of claim 26, in which the controller computes the first indicated pacing interval $(T_n)$ according to: $T_n = a \cdot w \cdot AA_n + (1-w) \cdot T_{n-1}$, if $AA_n$ is concluded by an intrinsic beat, otherwise $T_n$ is computed according to $T_n = b \cdot w \cdot AA_n + (1-w) \cdot T_{n-1}$, if $AA_n$ is concluded by a paced beat, where b is a coefficient.

29. The system of claim 28, in which at least one of a, b, and w is a function of heart rate.

30. The system of claim 26, further including a sensor, and in which the controller computes a second indicated pacing interval based on signals received from the sensor, and in which the atrial therapy circuit provides pacing therapy that is also based on the second indicated pacing interval.

31. A method, including:

obtaining A-A intervals between atrial beats;

computing a first indicated pacing interval based at least on a most recent A-A interval duration and an immediately preceding value of the first indicated pacing interval; and providing atrial pacing therapy at a rate that generally exceeds an intrinsic atrial heart rate, based on the first indicated pacing interval.

32. The method of claim 31, in which computing the first indicated pacing interval includes differently weighting at least one of (1) the most recent A-A interval duration, or (2) the immediately preceding value of the first indicated pacing interval, based on whether the most-recent A-A interval is concluded by a paced or sensed beat.

33. The method of claim 31, in which computing the first indicated pacing interval includes summing a first addend based on the most recent A-A interval duration and a second addend based on the immediately preceding value of the first indicated pacing interval, wherein at least one of the first and second addends is different if the most recent A-A interval is concluded by an intrinsic beat versus if the most recent A-A interval is concluded by a paced beat.

34. The method of claim 31, in which computing the first indicated pacing interval ($T_n$) is carried out according to $T_n = A \cdot AA_n + B \cdot T_{n-1}$, where A and B are coefficients, $AA_n$ is the most recent A-A interval duration, and $T_{n-1}$ is the immediately preceding value of the first indicated pacing interval.

35. A cardiac rhythm management system, including:

an atrial sensing circuit for sensing atrial beats;

a controller, obtaining A-A intervals between atrial beats and computing a first indicated pacing interval based at least on a most recent A-A interval duration and an immediately preceding value of the first indicated pacing interval; and an atrial therapy circuit, providing pacing therapy, at a rate that generally exceeds an intrinsic atrial heart rate, based on the first indicated pacing interval.

36. The system of claim 35, in which the controller adjusts the first indicated pacing interval, by differently weighting at least one of (1) the most recent A-A interval duration, or (2) the immediately preceding value of the first indicated pacing interval, if the most-recent A-A interval is concluded by a paced beat than if the most recent A-A interval is concluded by a sensed beat.

37. The system of claim 35, in which the controller computes the first indicated pacing interval ($T_n$) according to: $T_n = a \cdot w \cdot AA_n + (1-w) \cdot T_{n-1}$, if $AA_n$ is concluded by an intrinsic beat, otherwise $T_n$ is computed according to $T_n = b \cdot w \cdot AA_n + (1-w) \cdot T_{n-1}$, if $AA_n$ is concluded by a paced beat.

* * * * *